(12) United States Patent
Deng et al.

(10) Patent No.: US 11,499,163 B2
(45) Date of Patent: Nov. 15, 2022

(54) EXPRESSION METHOD OF HAEMOCOAGULASE ACUTUS (HALASE) RECOMBINANT PROTEIN

(71) Applicant: SUN YAT-SEN UNIVERSITY, Guangdong (CN)

(72) Inventors: Qin Deng, Guangdong (CN); Xiao Shen, Guangdong (CN); Weiwei Su, Guangdong (CN); Zhong Wu, Guangdong (CN); Wei Peng, Guangdong (CN); Yonggang Wang, Guangdong (CN)

(73) Assignee: SUN YAT-SEN UNIVERSITY, Guangzhou (CN)

( * ) Notice: Subject to any disclaimer, the term of this patent is extended or adjusted under 35 U.S.C. 154(b) by 1041 days.

(21) Appl. No.: 16/175,812

(22) Filed: Oct. 30, 2018

(65) Prior Publication Data

US 2019/0048361 A1 Feb. 14, 2019

Related U.S. Application Data

(63) Continuation-in-part of application No. PCT/CN2017/092327, filed on Jul. 10, 2017.

(51) Int. Cl.
| | |
|---|---|
| *C12N 15/85* | (2006.01) |
| *C12N 15/64* | (2006.01) |
| *G01N 33/573* | (2006.01) |
| *C12N 9/64* | (2006.01) |

(52) U.S. Cl.
CPC .......... *C12N 15/85* (2013.01); *C12N 9/6418* (2013.01); *C12N 15/64* (2013.01); *G01N 33/573* (2013.01); *G01N 2333/96422* (2013.01)

(58) Field of Classification Search
None
See application file for complete search history.

(56) References Cited

FOREIGN PATENT DOCUMENTS

| CN | 1986813 A | | 6/2007 | |
|---|---|---|---|---|
| CN | 102660565 | * | 9/2012 | ............. C12N 15/10 |
| CN | 102660565 A | | 9/2012 | |

OTHER PUBLICATIONS

Foti et al., "Conservation and Divergence of the Yeast and Mammalian Unfolded Protein Response" 274(43) The Journal of Biological Chemistry 30402-30409 (Year: 1999).*
Mauro et al., "A critical analysis of codon optimization in human therapeutics" 20(11) Trends in Molecular Medicine 604-613 (Year: 2014).*

\* cited by examiner

*Primary Examiner* — Nancy J Leith

(57) ABSTRACT

The disclosure relates to an expression method of a Haemocoagulase Acutus (Halase) recombinant protein. The method includes the following steps: (1) optimizing a halase gene; (2) performing Polymerase Chain Reaction (PCR) amplification on an optimized halase gene; (3) constructing an Agkis-pMCX expression vector, transforming plasmids to competent cells of an *Escherichia coli* for amplification, screening in an Amp-resistant manner for positive cloning, sequencing and extracting recombinant plasmids with correct sequencing; (4) transfecting recombinant plasmids to CHO cells; and (5) expressing the recombinant protein and identifying. According to the expression method, a recombinant halase is expressed first using the CHO cells cultured in a serum-free suspension manner; and by utilizing a bioengineering means, the actual production problems of insufficient raw material sources and unstable quality of a snake venom product are solved successfully.

9 Claims, 1 Drawing Sheet

Specification includes a Sequence Listing.

SEQUENCE LISTING

<160> NUMBER OF SEQ ID NOS: 16

<210> SEQ ID NO 1

<211> LENGTH: 756
<212> TYPE: DNA
<213> ORGANISM: Artificial Sequence
<220> FEATURE:
<223> OTHER INFORMATION: Synthetic

<400> SEQUENCE: 1

```
gactgcccca gcgactggag cagctacgag ggccactgct acaagccctt caacgagccc      60
aagaactggg ccgacgccga gaacttctgc accaagcagc acaccggcgg ccacctggtg     120
agcttccaga gcaccgagga ggccgacttc gtggtgaagc tggccttcca gaccttcgac     180
tacggcctgt tctggttcgg cctgagcaag ctgtggaacc agtgcaactg gcagtggagc     240
aacgccgcca tgctgaagta caccgactgg gccgaggaga gctactgcgt gtacttcaag     300
agcaccaaca acaagtggag gagcctgacc tgcaggatgc tggccaactt cgtgtgcgag     360
ttccaggccg actgcagcag cggctggagc agctacgagg ccactgcta caaggtgttc     420
aagcagagca agacctgggc cgacgccgag agcttctgca ccaagcaggt gaacggcggc     480
cacctggtga gcctggagag cagcggcgag gccgacttcg tgggccagct gctggcccag     540
aagctgaaga gcgccaagct gcacgtgtgg ctgggcctga gggcccagaa caaggagaag     600
cagtgcagcc tgcagtggag cgacggcagc agcctgagct acgagaactg gctggaggag     660
gagagcaaga agtgcctggg cgtgcacctg gagaccggct ccacaagtg ggagaacttc     720
tactgcgagc agcaggaccc cttcgtgtgc gaggcc                              756
```

<210> SEQ ID NO 2
<211> LENGTH: 60
<212> TYPE: DNA
<213> ORGANISM: Artificial Sequence
<220> FEATURE:
<223> OTHER INFORMATION: Synthetic

<400> SEQUENCE: 2

```
ctgctgcagc atgtcctcct gcatctcctc ctgctcccca tcgactgccc cagcgactgg      60
```

<210> SEQ ID NO 3
<211> LENGTH: 61
<212> TYPE: DNA
<213> ORGANISM: Artificial Sequence
<220> FEATURE:
<223> OTHER INFORMATION: Synthetic

<400> SEQUENCE: 3

```
atagcggccg catgtgggtg accaaactcc tgccagccct gctgctgcag catgtcctcc      60
t                                                                     61
```

<210> SEQ ID NO 4
<211> LENGTH: 55
<212> TYPE: DNA
<213> ORGANISM: Artificial Sequence
<220> FEATURE:
<223> OTHER INFORMATION: Synthetic

<400> SEQUENCE: 4

```
ttctgttggc aagttgctgg attatagtga ggagtgactg ccccagcgac tggag           55
```

<210> SEQ ID NO 5
<211> LENGTH: 56
<212> TYPE: DNA
<213> ORGANISM: Artificial Sequence
<220> FEATURE:
<223> OTHER INFORMATION: Synthetic

<400> SEQUENCE: 5
atagcggccg catgcccttg ctttggctga gaggatttct gttggcaagt tgctgg        56

<210> SEQ ID NO 6
<211> LENGTH: 55
<212> TYPE: DNA
<213> ORGANISM: Artificial Sequence
<220> FEATURE:
<223> OTHER INFORMATION: Synthetic

<400> SEQUENCE: 6
cattcctgat ggcagctgcc caaggtgtcg acgcagactg ccccagcgac tggag         55

<210> SEQ ID NO 7
<211> LENGTH: 56
<212> TYPE: DNA
<213> ORGANISM: Artificial Sequence
<220> FEATURE:
<223> OTHER INFORMATION: Synthetic

<400> SEQUENCE: 7
atagcggccg catggcttgg gtgtggacct tgccattcct gatggcagct gcccaa        56

<210> SEQ ID NO 8
<211> LENGTH: 53
<212> TYPE: DNA
<213> ORGANISM: Artificial Sequence
<220> FEATURE:
<223> OTHER INFORMATION: Synthetic

<400> SEQUENCE: 8
ttgctgctgc tgtggcttac aggtacgcgt tgtgactgcc ccagcgactg gag           53

<210> SEQ ID NO 9
<211> LENGTH: 56
<212> TYPE: DNA
<213> ORGANISM: Artificial Sequence
<220> FEATURE:
<223> OTHER INFORMATION: Synthetic

<400> SEQUENCE: 9
atagcggccg catgagtgtg ctcactcagg tcctggcgtt gctgctgctg tggctt        56

<210> SEQ ID NO 10
<211> LENGTH: 54
<212> TYPE: DNA
<213> ORGANISM: Artificial Sequence
<220> FEATURE:
<223> OTHER INFORMATION: Synthetic

<400> SEQUENCE: 10
ttgctgctgc tgtggcttac aggtacgcgt tgtgactgca gcagcggctg gagc          54

<210> SEQ ID NO 11
<211> LENGTH: 38
<212> TYPE: DNA
<213> ORGANISM: Artificial Sequence
<220> FEATURE:
<223> OTHER INFORMATION: Synthetic

<400> SEQUENCE: 11
ataggatcct tattaggcct cgcacacgaa ggggtcct                            38

<210> SEQ ID NO 12
<211> LENGTH: 38
<212> TYPE: DNA
<213> ORGANISM: Artificial Sequence
<220> FEATURE:
<223> OTHER INFORMATION: Synthetic

<400> SEQUENCE: 12
ataggatcca ttattggcct ggaactcgca cacgaagt                            38

<210> SEQ ID NO 13
<211> LENGTH: 369
<212> TYPE: DNA
<213> ORGANISM: Artificial Sequence
<220> FEATURE:
<223> OTHER INFORMATION: Synthetic

<400> SEQUENCE: 13
gactgcccca gcgactggag cagctacgag ggccactgct acaagccctt caacgagccc    60
aagaactggg ccgacgccga gaacttctgc accaagcagc acaccggcgg ccacctggtg   120
agcttccaga gcaccgagga ggccgacttc gtggtgaagc tggccttcca gaccttcgac   180
tacggcctgt tctggttcgg cctgagcaag ctgtggaacc agtgcaactg cagtggagc    240 aacgccgcca tgctgaagta caccgactgg gccgaggaga gctactgcgt gtacttcaag   300
agcaccaaca caagtggag gagcctgacc tgcaggatgc tggccaactt cgtgtgcgag    360
ttccaggcc                                                           369

<210> SEQ ID NO 14
<211> LENGTH: 387
<212> TYPE: DNA
<213> ORGANISM: Artificial Sequence
<220> FEATURE:
<223> OTHER INFORMATION: Synthetic

<400> SEQUENCE: 14
gactgcagca gcggctggag cagctacgag ggccactgct acaaggtgtt caagcagagc    60
aagacctggg ccgacgccga gagcttctgc accaagcagg tgaacggcgg ccacctggtg   120
agcctggaga gcagcggcga ggccgacttc gtgggccagc tgctggccca gaagctgaag   180
agcgccaagc tgcacgtgtg gctgggcctg agggcccaga acaaggagaa gcagtgcagc   240
ctgcagtgga gcgacggcag cagcctgagc tacgagaact ggctggagga ggagagcaag   300
aagtgcctgg gcgtgcacct ggagaccggc ttccacaagt gggagaactt ctactgcgag   360
cagcaggacc ccttcgtgtg cgaggcc                                       387

<210> SEQ ID NO 15
<211> LENGTH: 123
<212> TYPE: PRT
<213> ORGANISM: Artificial Sequence
<220> FEATURE:
<223> OTHER INFORMATION: Synthetic

<400> SEQUENCE: 15

Asp Cys Pro Ser Asp Trp Ser Ser Tyr Glu Gly His Cys Tyr Lys Pro
1               5                   10                  15

Phe Asn Glu Pro Lys Asn Trp Ala Asp Ala Glu Asn Phe Cys Thr Lys
            20                  25                  30

Gln His Thr Gly Gly His Leu Val Ser Phe Gln Ser Thr Glu Glu Ala
        35                  40                  45

```
Asp Phe Val Val Lys Leu Ala Phe Gln Thr Phe Asp Tyr Gly Leu Phe
    50                  55                  60
Trp Phe Gly Leu Ser Lys Leu Trp Asn Gln Cys Asn Trp Gln Trp Ser
 65              70                  75                      80
Asn Ala Ala Met Leu Lys Tyr Thr Asp Trp Ala Glu Glu Ser Tyr Cys
                 85                  90                  95
Val Tyr Phe Lys Ser Thr Asn Asn Lys Trp Arg Ser Leu Thr Cys Arg
                100             105             110
Met Leu Ala Asn Phe Val Cys Glu Phe Gln Ala
            115             120

<210> SEQ ID NO 16
<211> LENGTH: 129
<212> TYPE: PRT
<213> ORGANISM: Artificial Sequence
<220> FEATURE:
<223> OTHER INFORMATION: Synthetic

<400> SEQUENCE: 16

Asp Cys Ser Ser Gly Trp Ser Ser Tyr Glu Gly His Cys Tyr Lys Val
 1               5                  10                  15
Phe Lys Gln Ser Lys Thr Trp Ala Asp Ala Glu Ser Phe Cys Thr Lys
                20                  25                  30
Gln Val Asn Gly Gly His Leu Val Ser Leu Glu Ser Ser Gly Glu Ala
            35                  40                  45
Asp Phe Val Gly Gln Leu Leu Ala Gln Lys Leu Lys Ser Ala Lys Leu
    50                  55                  60
His Val Trp Leu Gly Leu Arg Ala Gln Asn Lys Glu Lys Gln Cys Ser
 65              70                  75                      80
Leu Gln Trp Ser Asp Gly Ser Ser Leu Ser Tyr Glu Asn Trp Leu Glu
                85                  90                  95
Glu Glu Ser Lys Lys Cys Leu Gly Val His Leu Glu Thr Gly Phe His
                100             105             110
Lys Trp Glu Asn Phe Tyr Cys Glu Gln Gln Asp Pro Phe Val Cys Glu
            115             120             125
Ala
```

EXPRESSION METHOD OF HAEMOCOAGULASE ACUTUS (HALASE) RECOMBINANT PROTEIN

CROSS-REFERENCE TO RELATED APPLICATION

The present application is a continuation-in-part application of PCT Application No. PCT/CN2017/092327 filed on Jul. 10, 2017, the disclosure of which is hereby incorporated by reference in their entirety.

REFERENCE TO SEQUENCE LISTING

The Sequence Listing is submitted as an ASCII formatted text file via EFS-Web, with a file name of "Sequence_listing.TXT", a creation date of Oct. 29, 2018, and a size of 7,079 bytes. The Sequence Listing filed via EFS-Web is part of the specification and is incorporated in its entirety by reference herein.

TECHNICAL FIELD

The disclosure relates to an expression method of a Haemocoagulase Acutus (Halase) recombinant protein.

BACKGROUND

A Haemocoagulase Acutus (hereinafter referred to as a halase) is a novel hemostatic drug researched and developed by our team and is a batroxobin separated from snake venom of an agkistrodonacutus and purified. It has a relatively strong hemostatic effect and is safe and nontoxic.

At present, a source of a venomous snake mainly lies in two manners, namely artificial feeding and wild catching. Due to different factors such as geographical conditions and feeding conditions, there are huge differences in components and properties of snake venoms, thereby bringing a certain difficulty to scale production and making homogeneity of a product restricted. Along with the development of a bioengineering technology, it is an important direction for research and development of SVTLEs drugs to develop a Snake Venom Thrombin-Like Enzymes (SVTLEs) recombinant protein product to replace these drugs, in hoping to stably express the SVTLEs product having good physiological activity via a protein engineering means.

An expression system of a SVTLEs recombinant protein is constructed via a prokaryotic expression system at the earliest. Glycosylation modifying conditions of SVTLEs may be different, but most SVTLEs are glycoproteins, the contents are between 0% and 30% and the content of a special type is even up to 40% or more. However, a common expression strain for bacteria does not have a glycosylation capacity, which will greatly affect the activity of the protein. Moreover, an *Escherichia coli* is expressed mostly in a form of an inclusion body and it is common for a researcher to add a Thioredoxin (TrxR) marker to increase soluble expression of a heterologous protein. In the prokaryotic expression system, a yeast expression system which is relatively mature is also used to express the SVTLEs recombinant protein. Nevertheless, the yeast expression system may have excessive glycosylation modification for the expression of the heterologous protein, or lacks modification for a complex glycosyl chain, all of which will affect the functions of the recombinant protein.

A mammal cell expression system has a higher glycosylation mechanism and thus gradually becomes an important system to express a heterogenous glycoprotein. In the mammal cell expression system, CHO cells have become a most important expression system in the biopharmaceutical field. With the development of a serum-free suspension culture technology, limitations that the traditional mammal cell expression system is infected by a virus easily and has a low automation level are greatly improved, and thus the system is more suitable for industrial large-scale production. Therefore, the applications of the system are expanded continuously and such a system is widely applied to researching and developing biopharmaceutical products such as an antibody, a vaccine and a recombinant protein drug. In 2010, U.S. Food and Drug Administration approved that a CHO expression protein could be used as a drug directly.

SUMMARY

In order to solve the above technical problems, the disclosure discloses an expression method of a halase recombinant protein. The halase recombinant protein is expressed first using CHO cells via a serum-free suspension culture technology. The method includes the following steps:

(1) optimizing a halase gene;
(2) performing Polymerase Chain Reaction (PCR) amplification on an optimized gene;
(3) constructing an expression vector;
(4) transfecting recombinant plasmids to CHO cells; and
(5) expressing the recombinant protein and identifying.

Wherein, in the step (3), a method for constructing the expression vector specifically is as follows: cutting a recycled PCR product and a pMCX cloning vector by an enzyme and connecting, constructing Agkis-pMCX plasmids, transforming the Agkis-pMCX plasmids to competent cells of an *Escherichia coli* for amplification, screening in an Amp-resistant manner for positive cloning and sequencing; and extracting recombinant plasmids with correct sequencing.

A method for performing cutting the PCR product and the pMCX cloning vector by the enzyme and connecting preferably is as follows: performing endonuclease digestion on amplified halase genes and connecting a gene target segment to the expression vector using a T4 ligase.

In the step (4), a method for transfecting the recombinant plasmids to the CHO cells specifically is as follows: taking an appropriate amount of cells, centrifuging and resuspending using a fresh solution, so that a final density of the cells is 5 mioc/mL; during centrifugation, premixing plasmid DNA with PEI and incubating at a room temperature; adding a treated DNA&PEI mixture to the prepared cells, uniformly mixing and culturing at 31° C.; transfecting, adding an appropriate amount of DMSO, shaking to mix uniformly and culturing at 31° C.; and after transfecting, taking a sample for detection; wherein, the recombinant plasmids containing a protein gene full length are transinfected independently and the recombinant plasmids containing an A sub-gene sequence and a B sub-gene sequence are co-transfected to the CHO cells.

A specific method of the step (1) includes the following steps:

1) optimizing a halase gene sequence according to an encoding preference of a mammal;
2) designing upstream primers and downstream primers according to a synthesized halase gene, two enzyme-cut sites of Not I and BamH I being introduced to the primers, and additionally, a segment of secreted signal peptide sequence being further added; and (3) since the gene includes two sub-gene sequences of an A sub-gene and a B sub-gene of the protein, adjusting the upstream and downstream primers so that the protein gene sequence full length, the A sub-gene sequence and the B sub-gene sequence can be amplified respectively (Subunit A gene sequence consists of nucleotide bases 1-369 of SEQ ID NO:1. Subunit A gene sequence as shown in SEQ ID NO:13, and it's protein sequence as shown in SEQ ID NO:15. Subunit B sequence consists of nucleotide bases 370-756 of SEQ ID NO:1. Subunit B gene sequence as shown in SEQ ID NO:14, and it's protein sequence as shown in SEQ ID NO:16).

Compared with the conventional art, a recombinant halase is expressed first using the CHO cells cultured in a serum-free suspension manner; and by utilizing a bioengineering means, the actual production problems of insufficient raw material sources and unstable quality of a snake venom product are solved successfully.

DETAILED DESCRIPTION

Figure 1:
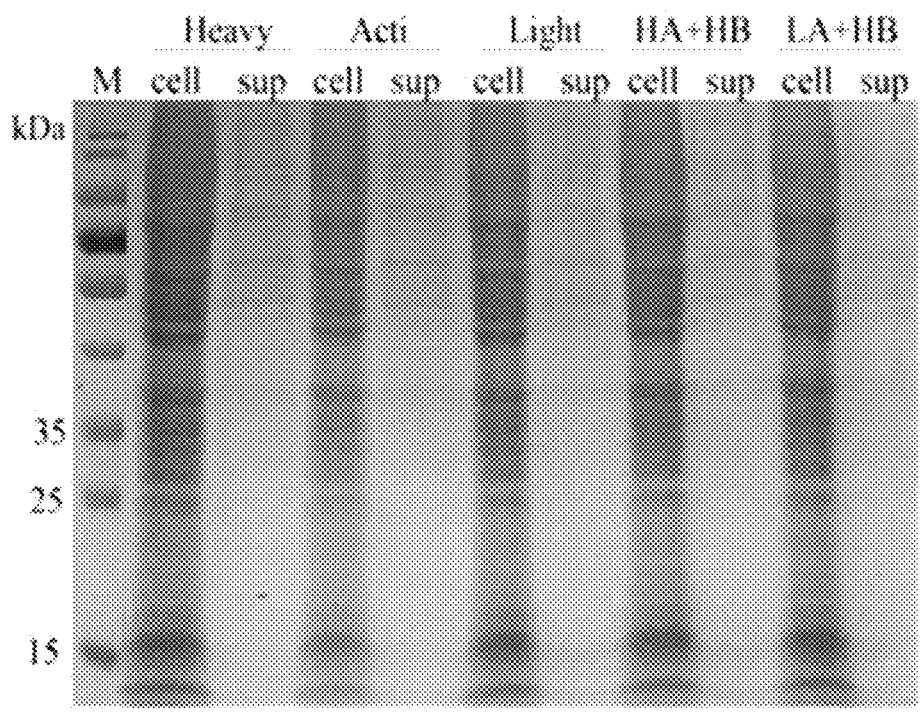
FIG. 1 is a schematic diagram of SDS-PAGE electrophoresis of a recombinant halase according to an embodiment of the disclosure.

The disclosure will be further described below with reference to specific embodiments.

Embodiment: an operation method for expressing a halase recombinant protein

1. Experimental Materials 1.1 Experimental Instruments

A PCR instrument: Bio-Rad Company; an electrophoresis apparatus: Beijing Junyi Dongfang Electrophoresis Equipment Co., Ltd.; a gel imaging system: Zhuhai Heima Medical Instrument Co., Ltd.; a gel cutter: Hangzhou Miu Instruments Co., Ltd.; a constant temperature mixer: Hangzhou Miu Instruments Co., Ltd.; an ultramicro ultraviolet and visible spectrophotometer: American Quawell Company; a 2-8° C. refrigerated container: Zhongke Meiling Cryogenics Co., Ltd.; a −20° C. medical low temperature container: Zhongke Meiling Cryogenics Co., Ltd.; a three-hole electrothermal constant-temperature water bath: Shanghai Hengyi Science Instrument Co., Ltd.; a bacteriological incubator: Shanghai Hengyi Science Instrument Co., Ltd.; a horizontal full-temperature shaking incubator: Shanghai Zhichu Instruments Co., Ltd.; a cell culture shaker: Adolf Kuhner Company; an ultrasonic cell crusher: Ningbo Scientz Biotechnology Co., Ltd.; a magnetic stirrer: Wiggens Company; a pH meter: Ohaus Instrument (Shanghai) Co., Ltd.; a double purification workbench: Shanghai Sujing Industry Co., Ltd.; a transfer printing system: Bio-Rad Company; a vertical electrophoresis system: Bio-Rad Company; a decolourization shaker: Shanghai Tanon Science & Technology Co., Ltd.; and an autoclave: Shanghai ShenAn Medical instrument Factory.

1.2 Experiment Reagents

An expression carrier pMCX, an *Escherichia coli* DH5 α and CHO DG44 cells all are prepared and provided by Guangzhou Cantonbio Co., Ltd.; a KOD DNA polymerase: Toyobo (Shanghai) Biotech Co., Ltd.; a T4 DNA ligase: Novoprotein Scientific Inc.; a restriction endonuclease NotI: Thermo Fisher Scientific Company; a restriction endonuclease BamHI: Thermo Fisher Scientific Company; a plasmid extraction kit: American OMEGA Company; a DNA agarose gel recovery kit: American OMEGA Company; a DNA Marker: Thermo Fisher Scientific Company; a CHO culture medium: Lonza Company; DMSO: Tianjin No. 1 Chemical Reagent Factory; PEI: Sigma Aldrich Company; a Trypan Blue dyeing liquor: Sigma Aldrich Company; a specific polyclonal antibody: Cloud-clone Company; a rabbit IgG antibody: Proteintech Company; ampicillin: Sangon Biotech Co., Ltd.; agar powder: Guangdong Huankai Microbial Sci.&Tech, Co., Ltd.; yeast extract powder: Oxoid Company; and a peptone: Oxoid Company.

2. Experimental Methods 2.1 Gene Amplification

Through a Java Codon Adaptation Tool (JCAT), a halase protein sequence is translated into a DNA sequence. The sequence is optimized according to an encoding preference of a mammal and an optimized gene sequence is synthesized by Guangzhou IGE Biotechnology Ltd, as shown in SEQ ID NO: 1.

Upstream primers and downstream primers are designed according to the synthesized halase gene. Two enzyme-cut sites of Not I and BamH I are introduced to the primers. And additionally, a segment of secreted signal peptide sequence is further added, see Table 1 and the sequence (from SEQ ID NO:2 to SEQ ID NO:12).

TABLE 1

| PCR primers of recombinant halase (SEQ ID NOs: 2-12) ||||
| --- | --- | --- |
| Signal peptide | Primers | Sequences (5' → 3') |
|  | Forward primers |  |
| HGFs | HGF-Agkis-AB-F1 | CTGCTGCAGCATGTCCTCCTGCATCTCCTCCTGCTCCCC ATCGACTGCCCCAGCGACTGG |
|  | HGF-Agkis-AB-F2 | ATAGCGGCCGCATGTGGGTGACCAAACTCCTGCCAGCC CTGCTGCTGCAGCATGTCCTCCT |
| Actin A | Acti-Agkis-AB-F1 | TTCTGTTGGCAAGTTGCTGGATTATAGTGAGGAGGAC TGCCCCAGCGACTGGAG |
|  | Acti-Agkis-AB-F2 | ATAGCGGCCGCATGCCCTTGCTTTGGCTGAGAGGATTT CTGTTGGCAAGTTGCTGG |
| Heavy chain | Heavy-Agkis-AB-F1 | CATTCCTGATGGCAGCTGCCCAAGGTGTCGACGCAGAC TGCCCCAGCGACTGGAG |
|  | Heavy-Agkis-AB-F2 | ATAGCGGCCGCATGGCTTGGGTGTGGACCTTGCCATTC CTGATGGCAGCTGCCCAA |

TABLE 1-continued

PCR primers of recombinant halase (SEQ ID NOs: 2-12)

| Signal peptide | Primers | Sequences (5' → 3') |
|---|---|---|
| Light chain | Light-Agkis-AB-F1 | TTGCTGCTGCTGTGGCTTACAGGTACGCGTTGTGACTG CCCCAGCGACTGGAG |
| | Light-Agkis-AB-F2 | ATAGCGGCCGCATGAGTGTGCTCACTCAGGTCCTGGCG TTGCTGCTGCTGTGGCTT |
| | Light-Agkis-B-F1 | TTGCTGCTGCTGTGGCTTACAGGTACGCGTTGTGACTG CAGCAGCGGCTGGAGC |
| Reverse primers | | |
| | Agkis-AB-R | ATAGGATCCTTATTAGGCCTCGCACACGAAGGGGTCCT |
| | Agkis-A-R | ATAGGATCCATTATTGGCCTGGAACTCGCACACGAAGT |

The gene sequence includes two sub-gene (A and B) sequences of the protein. Through adjusting the upstream and downstream primers, a protein gene sequence full length, an A sub-gene sequence and a B sub-gene sequence can be respectively amplified. PCR amplification is performed on the synthesized gene and a PCR product is recovered using agarose gel electrophoresis.

Endonuclease digestion is performed on the amplified halase gene and a gene target segment is connected to the expression vector using the T4 ligase. An Amp (Ampicillin) is selected as a screening antibiotic.

2.2 Expression Vector Construction

The recovered PCR product and the pMCX cloning vector are cut by an enzyme and are connected to construct Agkis-pMCX plasmids. The Agkis-pMCX plasmids are transformed to competent cells of an *Escherichia coli* for amplification, are screened in an Amp-resistant manner for positive cloning and are sent to Guangzhou IGE Biotechnology Ltd. for sequencing. The recombinant plasmids with correct sequencing are extracted and are used in a sequent CHO cell transfection test.

2.3 CHO Cell Transfection

On the same day of transfection, a cell density (mioc/mL) is recorded and an appropriate amount of cells is taken and is centrifuged for 3 min at 1300 rpm. A fresh solution (31° C., preheated in advance) is used for resuspension so that the final cell density is 5 mioc/mL. During centrifugation, plasmid DNA and PEI are premixed in a clean centrifugal pipe, are blown and beaten slightly and are incubated for 3-5 min at a room temperature. A treated DNA & PEI mixture is added to prepared cells, is shaken to mix uniformly and is cultured at 31° C. After 10 min of the transfection, an appropriate amount of DMSO is added, is shaken to mix uniformly and is cultured at 31° C. After the transfection, a sample is taken to detect. Wherein, the recombinant plasmids containing the protein gene full length are independently transfected, and the recombinant plasmids containing the A sub-gene sequence and the B sub-gene sequence are co-transfected to the CHO cells.

2.4 Protein Expression and Identification (1) Sample Preparation

80 µl of cells cultured for several days is taken and is centrifuged for 3 min at 1300 rpm, a supernatant and the cells are respectively collected to precipitate, about 80 µl of supernatant is taken and is added to 20 µl of 5× loading buffer to mix uniformly, after 80 µl 1×PBS (pH7.5) of buffer is added to the cells to resuspend the cells, 20 µl (reduced) of 5× loading buffer is added to mix uniformly, the sample is boiled for 8 min at 100° C. and is centrifugated for 1 min at 1200 rpm for later use/is stored at a −20° C. refrigerator.

(2) SDS-PAGE

Electrophoresis on a first piece of gel: 15 µl of polyacrylamide gel which is prepared in advance and whose concentration is 12% is loaded to each pore, and after running is operated at 80V of voltage till the sample has a spacer gel and after the voltage is adjusted to 120V, the electrophoresis is performed for 90 min. Electrophoresis on a second piece of gel: 15 µl of polyacrylamide gel which is prepared in advance and whose concentration is 12% is loaded to each pore, and after running is operated at 80V of voltage till the sample has a spacer gel and after the voltage is adjusted to 120V, the electrophoresis is performed for 90 min. As shown in FIG. 1, the M is a protein marker, the cell is a cell broken liquid, and the sup is a cell culture supernate.

(3) Western Blot

Figure 2:
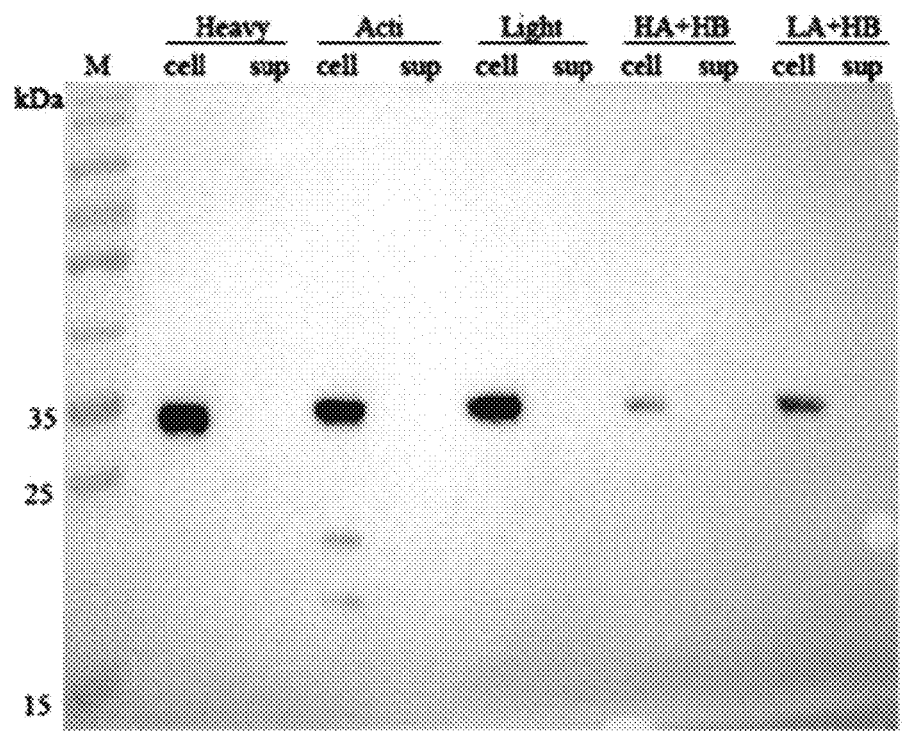
FIG. 2 is a schematic diagram of Western Blot of a recombinant halase according to an embodiment of the disclosure.

Membrane transfer is performed for 40 min at 80 mA, and 5% of skimmed milk powder is added and is sealed for 1 h at a room temperature. A specific antibody is incubated for 2 h at the room temperature according to a proportion of 1:5000; TBST is used to clean for 3 times, 5 min for each; a rabbit anti-IgG antibody is incubated for 1 h at the room temperature; PBST is used to clean for 3 times, 5 min for each; and the membrane is developed with ECL, is exposed for 1 min and is photographed. As shown in FIG. 2, M is a protein marker, the cell is a cell broken liquid, and the sup is a cell culture supernate.

3. Experiment Result

As shown in an SDS-PAGE electrophoretogram, a protein close to a molecular weight of a target protein is respectively detected in cell broken liquids containing six recombinant vectors such as HGFs, Heavy, Acti, Light, HA+HB and LA+HB and there is nearly no visible strip in the cell culture supernate. With further detection and identification of Western Blot, in addition to HGFs, the expression of the target protein is detected in the cell broken liquids containing the five recombinant vectors such as the Heavy, the Acti, the Light, the HA+HB and the LA+HB and the molecular weight is about 32 kDa, and no visible strip is seen in the cell culture supernate.

The invention claimed is:

1. A method of isolating a recombinant Haemocoagulase Acutus (Halase) protein comprising: (1) obtaining an optimized Halase gene comprising the sequence of SEQ ID NO:1; (2) inserting the optimized Halase gene into a mammalian expression vector; (3) transfecting the expression vector into a CHO cell; (4) culturing the transfected CHO cell in a serum-free medium, wherein the CHO cell expresses the recombinant Halase protein; and (5) isolating the recombinant Halase protein from the CHO cell.

2. The method of claim 1, wherein after (1) and before (2) the optimized Halase is amplified with PCR.

3. The method of claim 1, wherein the mammalian expression vector is a pMCX cloning vector.

4. A method of isolating a recombinant Haemocoagulase Acutus (Halase) protein comprising: (1) independently obtaining an optimized Halase gene subunit A comprising the sequence of SEQ ID NO: 13 and an optimized Halase gene subunit B comprising the of SEQ ID NO: 14; (2) independently inserting each of the subunit A and subunit B into a mammalian expression vector to obtain plasmid 1 and plasmid 2 respectively; (3) co-transfecting plasmid 1 and plasmid 2 into a CHO cell; (4) culturing the transfected CHO cell in a serum-free medium, wherein the CHO cell expresses the recombinant Halase protein; and (5) isolating the recombinant Halase protein from the CHO cell.

5. The method of claim 4, wherein after (1) and before (2) the optimized Halase subunit A and subunit B are independently amplified with PCR.

6. The method of claim 4, wherein the mammalian expression vector is a pMCX cloning vector.

7. An expression vector comprising a nucleotide sequence selected from the group consisting of SEQ ID NO:1, SEQ ID NO: 13 and SEQ ID NO: 14.

8. The expression vector of claim 7, wherein the expression vector is a mammalian expression vector.

9. The expression vector of claim 8, wherein the mammalian expression vector is a pMCX cloning vector.

* * * * *